(12) United States Patent
Dominique et al.

(10) Patent No.: US 6,685,966 B1
(45) Date of Patent: Feb. 3, 2004

(54) COMPOSITE PARTICLES CONTAINING AN ACTIVE SUBSTANCE

(75) Inventors: Dupuis Dominique, Deuil-la-Barre (FR); Reeb Roland, Gressy (FR)

(73) Assignee: Rhodia Chimie, Courbevoie Cedex (FR)

( * ) Notice: Subject to any disclaimer, the term of this patent is extended or adjusted under 35 U.S.C. 154(b) by 0 days.

(21) Appl. No.: 09/622,207

(22) PCT Filed: Feb. 12, 1999

(86) PCT No.: PCT/FR99/00321

§ 371 (c)(1),
(2), (4) Date: Sep. 27, 2000

(87) PCT Pub. No.: WO99/41298

PCT Pub. Date: Aug. 19, 1999

(30) Foreign Application Priority Data

Feb. 13, 1998 (FR) .............................................. 98 01780

(51) Int. Cl.$^7$ ............................ A61K 9/16; A61K 6/00; A61K 47/00
(52) U.S. Cl. ...................... 424/490; 424/401; 424/439; 424/497
(58) Field of Search ................................ 424/490, 497, 424/401, 439, 450

(56) References Cited

U.S. PATENT DOCUMENTS

| 4,474,852 A | * | 10/1984 | Craig | .......................... 428/403 |
| 5,372,804 A | | 12/1994 | Khoshdel et al. | .............. 424/59 |
| 6,136,891 A | * | 10/2000 | Chopin et al. | .............. 523/204 |
| 6,277,408 B1 | * | 8/2001 | Wellinghoff et al. | ........ 424/473 |

FOREIGN PATENT DOCUMENTS

| EP | 0 211 298 | | 2/1987 |
| WO | 97/32920 | * | 9/1997 |

* cited by examiner

Primary Examiner—Thurman K. Page
Assistant Examiner—S. Tran
(74) Attorney, Agent, or Firm—Burns, Doane, Swecker & Mathis, L.L.P.

(57) ABSTRACT

Composite particles are provided comprising at least one core including at least one organic polymer in which is dispersed at least one hydrophobic active material. The hydrophobic active material is a cosmetic, pharmaceutical, food or plant-protection material. The composite particles also include one external coating including at least one oxide and/or hydroxide of aluminum, of silicon, of zirconium and/or of a transition metal and one intermediate layer, present at least partially between the core and the external coating and including at least one alkaline earth metal hydroxide.

50 Claims, 1 Drawing Sheet

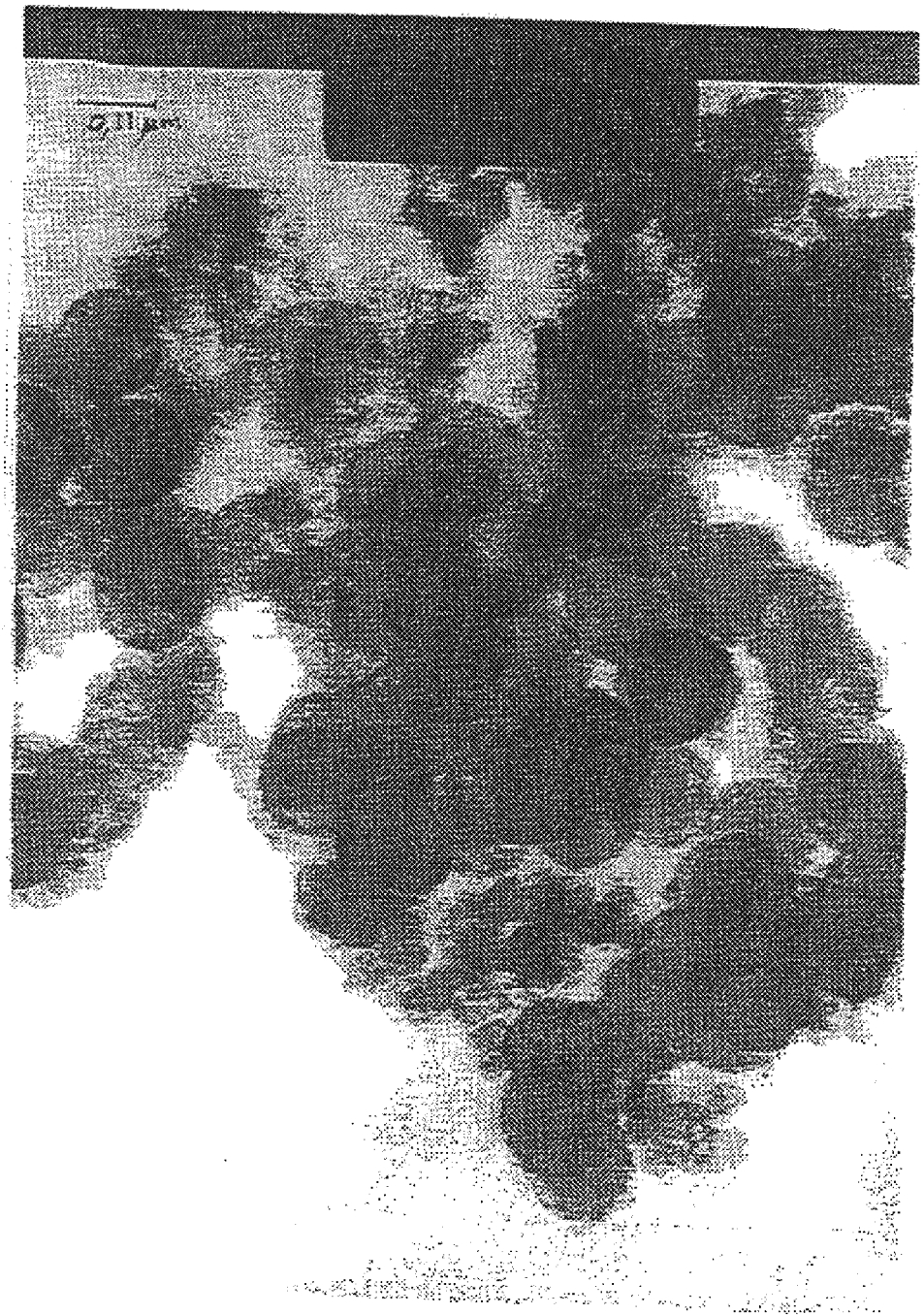

COMPOSITE PARTICLES CONTAINING AN ACTIVE SUBSTANCE

A subject-matter of the present invention is composite particles comprising a core based on at least one organic polymer in which is dispersed at least one hydrophobic organic material and an inorganic external coating.

More specifically, the present invention is targeted at the development of an encapsulation system appropriate for the packaging of a hydrophobic active material and for its release in a controlled way.

Encapsulation systems for active materials have already been developed. Mention may very particularly be made, as illustration of these, of those employing specific polymer materials as vehicle for active materials(s). They can be in particular latex microparticles in which the said active materials are dispersed.

However, this encapsulation system is not entirely satisfactory, in so far as it does not make it possible to guarantee that the active material which it comprises will be fully protected with respect to the external environment and vice versa. The fact that the active material is uniformly dispersed within the particles implies that this active material is present at the core of the particle but also at its periphery. As regards more particularly the active material present at the periphery, it is clear that it is exposed at least partially to the external environment. Thus, it remains vulnerable to any physicochemical variation in this environment, such as, for example, modification in pH, temperature or luminosity. It is obvious that this can be reflected by chemical transformations in the accessible active material and/or can contribute to its diffusion outside the particle.

Consequently, this type of encapsulation is not entirely satisfactory in terms of protection of the active material or of control of its release.

The object of the present invention is specifically to provide a novel encapsulation system which makes it possible to eliminate the problems mentioned above.

The invention is targeted at providing composite particles comprising an organic core, the active material(s) being dispersed in the core and this core being isolated from the external environment by a coating of inorganic nature.

This coating or alternatively shell advantageously makes it possible to meet the requirements mentioned above. It guarantees that the active material encapsulated in the organic core is protected with respect to the external environment and makes it possible, if appropriate, to control its diffusion by virtue of the specific choice of the components of this inorganic shell.

A first subject-matter of the present invention is thus composite particles comprising at least
- one core composed of at least one organic polymer in which is dispersed at least one hydrophobic active material,
- one external coating comprising at least one oxide and/or hydroxide of aluminium, of silicon, of zirconium and/or of a transition metal and
- one intermediate layer, present at least partially between the core and the external coating and comprising at least one alkaline earth metal hydroxide.

Another subject-matter of the invention is a process of use in the preparation of the abovementioned composite particles.

The claimed composite particles thus advantageously have a shell of inorganic nature. This inorganic shell is composed of at least two superimposed layers, a layer referred to as an intermediate layer and a layer referred to as an external coating layer. The main function of the intermediate layer is to strengthen the adhesion between the core of organic nature and the outermost layer of inorganic nature.

The coating (or, without distinction, the shell of the external layer) based on oxide and/or on hydroxide may only partially cover or may completely cover each core of organic polymer. It is also possible for this coating to be partially embedded in the intermediate layer covering the core of organic polymer, indeed even in the organic core when the latter is only partially covered with the intermediate layer.

The nature of the organic polymers constituting the core of the composite particles is preferably of the type of that of latex particles, that is to say of (co)polymer particles resulting from conventional processes for the emulsion (co)polymerization of copolymerizable organic monomers.

More generally, this polymer derives from at least one water-immiscible ethylenically unsaturated monomer which can be polymerized by the radical route.

Mention may in particular be made, by way of illustration of the monomers which are suitable for the invention, of vinylaromatic monomers, alkyl esters of $\alpha,\beta$-ethylenically unsaturated acids, vinyl esters of carboxylic acids, vinyl or vinylidene halides, conjugated aliphatic dienes and $\alpha,\beta$-ethylenically unsaturated nitriles.

Mention may in particular be made, by way of illustration of monomers of this type, of styrene, butadiene, acrylonitrile, chloroprene, vinyl or vinylidene chloride, isoprene, isobutylene, vinyl acetate, propylene, butylene and vinylpyrrolidone.

According to a specific form of the invention, the polymer can be a crosslinked polymer. This crosslinking is obtained by incorporation of a crosslinking agent, such as divinylbenzene, ethylene glycol dimethacrylate (EGDIM), allyl methacrylate or methylenebisacrylamide, during the synthesis of the said polymer. The choice of the crosslinking agent is made according to the nature of the monomers under consideration.

The polymer constituting the core of the composite particles according to the invention can also comprise up to 8%, preferably up to 4%, of at least one comonomer carrying ionogenic groups which can be polymerized by the radical route. The comonomer can in particular be a monomer selected from $\alpha,\beta$-ethylenically unsaturated carboxylic acids, sulphonated ethylenic monomers, hydroxyalkyl esters of $\alpha,\beta$-ethylenically unsaturated acids, amides of $\alpha,\beta$-ethylenically unsaturated acids and aminoesters of $\alpha,\beta$-ethylenically unsaturated acids.

Mention may very particularly be made, as examples of these ionogenic groups, of those selected from acrylic, methacrylic, itaconic, maleic, crotonic, para-styrenesulphonic, vinylsulphonic, 2-methacryloyl-oxyethylsulphonic, 2-acrylamido-2-methylpropane-sulphonic and vinylbenzenesulphonic acids, hydroxyethyl acrylate, hydroxyethyl methacrylate, acrylamide, methacrylamide and diethylaminoethyl methacrylate.

The polymer preferably does not comprise monomers with carboxyl or sulpho functional groups.

This polymer is more preferably selected from polystyrenes or copolymers of styrene and of acrylic esters, of styrene and of butadiene or of styrene, of butadiene and of acrylamide.

Mention may more particularly be made of the copolymers of styrene with acrylates or butadiene. They can advantageously be selected from butadiene-styrene copolymers, acrylic copolymers and butadiene-styrene-acrylamide copolymers.

These organic polymers more particularly exhibit a glass transition temperature of between −100° C. and 150°C. According to a particularly advantageous and preferred embodiment of the invention, the glass transition temperature is between −100°C. and 100°C. and more preferably between −150°C. and 100° C.

The polymers which can be employed according to the invention have a particle size of between 0.02 and 5 μm and preferably between 0.19 and 0.3 μm.

The diameter of the core of organic polymer incorporating the active material can generally vary between approximately 0.03 and 10 μm. It is more preferably of the order of 0.1 to 1 μm.

As regards the external coating of the claimed composite particles, it is composed of at least one oxide and/or hydroxide of aluminium, of silicon, of zirconium and/or of a transition metal.

The term "transition metal" is understood to mean more particularly the metals from the fourth period ranging from scandium to zinc, in so far as the latter are compatible in terms of harmlessness with the targeted application. They are more particularly a titanium, manganese, iron, cobalt, nickel or copper oxide and/or hydroxide.

The oxides and/or hydroxides of silicon, aluminium, titanium and zirconium are particularly well suited to the invention.

It should be noted that this coating can comprise an oxide and/or a hydroxide of just one or of several elements in the same layer. In particular, mixed oxides, such as, for example, an aluminosilicate, can be involved.

According to a first alternative form of the present invention, the external coating according to the invention is composed of a single layer based on at least one oxide and/or hydroxide of aluminium, of silicon, of zirconium and/or of a transition metal.

According to a second alternative form of the present invention, this external coating comprises at least two layers based on at least one oxide and/or hydroxide of aluminium, of silicon, of zirconium and/or of a transition metal. In such a case, the two superimposed layers, at least partially covering the core of the composite particles and themselves being at least partially covered, can be based on one or more oxides and/or hydroxides as identified above.

As was indicated previously, the composite particles according to the invention additionally exhibit a layer, known as an intermediate layer, at least partially covering the organic polymer particles described above.

This intermediate layer advantageously makes it possible to strengthen the attachment of the inorganic external coating described above to the surface of the organic core.

It is generally composed of one or more alkaline earth metal hydroxides. The hydroxides can in particular be calcium hydroxide and/or magnesium hydroxide.

The total thickness of the coating applied at the surface of the organic core of the claimed particles, that is to say comprising one or more layers based on at least one oxide and/or hydroxide of aluminium, of silicon, of zirconium and/or of a transition metal and a layer of at least one alkaline earth metal hydroxide, is generally at most 300 nm. It is usually at least 1 nm. More particularly, it is between 1 and 300 nm and preferably between 5 and 100 nm.

The active materials which can be incorporated within the organic polymer constituting the core of the claimed particles are preferably hydrophobic compounds. They can in particular be cosmetic, pharmaceutical, food or plant-protection active materials.

The particulate encapsulation system developed according to the invention is especially particularly advantageous in the application of cosmetic agent(s), which are generally very hydrophobic.

Mention may in particular be made, by way of illustration of these hydrophobic active materials, of organic UV stabilizers, essential or therapeutic oils, fragrances and cosmetic colorants.

Mention may very particularly be made, among organic UV stabilizers, of compounds of benzophenone type, methanedibenzoyl derivatives and cinnamic derivatives. It can in particular be 2-ethylhexyl methoxycinnamate, sold as UV-B stabilizer under the name Parsol MCX®.

The amount of active material dispersed within the organic polymer depends, of course, on its nature, on the recommended method of administration and on the subject treated.

By way of indication, this active material can be dispersed within the organic polymer in a proportion of 0.1 to 200% by weight, expressed with respect to the weight of dry polymer.

For example, a UV stabilizer can be dispersed in the organic polymer in a proportion of 0.1 to 200% by weight with respect to the weight of dry polymer.

The composite particles according to the invention preferably exhibit a specific surface of between approximately 1 and 200 $m^2/g$, preferably between approximately 1 and 100 $m^2/g$.

The term "specific surface" is understood to mean the BET specific surface, determined by nitrogen adsorption in accordance with ASTM Standard D 3663–78 drawn up from the Brunauer-Emmett-Teller method described in the periodical "The Journal of the American Chemical Society", 60, 309 (1938).

This specific surface can reveal the more or less smooth appearance of the coating which coats the organic polymer.

Their diameter can generally vary between approximately 0.02 and 6 μm and preferably between 0.1 and 0.4 μm.

A second subject-matter of the present invention is a process of use in the preparation of composite particles in accordance with the present invention.

More specifically, the claimed process is characterized in that it comprises at least:

the incorporation of at least one hydrophobic active material in particles based on at least one organic polymer, the said particles being in aqueous, alcoholic or aqueous/alcoholic dispersion and, if appropriate, formed in conjunction with the incorporation of the said active material, the dissolution of at least one alkaline earth metal salt in the liquid phase of the dispersion of polymer particles, which particles comprise at least one hydrophobic active material and are obtained according to the preceding stage, the addition of a base in a sufficient amount to precipitate a layer of oxide or of hydroxide of the said alkaline earth metal at the surface of the said particles, the bringing of at least one water-soluble silicon, aluminium, zirconium and/or transition metal salt into contact, in the liquid phase of the particle dispersion obtained on conclusion of the preceding stage, with at least one agent capable of reacting with the said soluble salt to form a precipitate composed of the corresponding oxide or hydroxide at the surface of the said particles and, the drying and the recovery of the composite particles thus obtained.

As mentioned above, the incorporation of active material in the aqueous dispersion of particles based on at least one organic polymer can be carried out according to two alternative forms. The active material can be introduced either before carrying out the radical emulsion polymerization of the monomers or on conclusion of this polymerization.

The polymerization per se of the monomers from which the organic polymer derives can be carried out conventionally.

The particles based on at least one organic polymer are obtained by aqueous, alcoholic or aqueous/alcoholic -radical emulsion polymerization of water-immiscible and polymerizable ethylenically unsaturated monomers.

The polymerization is preferably carried out in emulsion in water.

To this end, at least one emulsifier is employed. The latter can be either anionic or nonionic.

Mention may be made, as regards anionic emulsifiers which may be suitable for the present invention, of salts of fatty acids; alkaline alkyl sulphates, alkylsulphonates, alkylarylsulphonates, alkyl sulphosuccinates or alkyl phosphates; alkyl sulphosuccinates; sulphonates of alkylphenol polyglycol ethers; condensation products of fatty acids with oxy- and aminoalkanesulphonic acids; sulphated derivatives of polyglycol ethers; sulphated esters of fatty acids and of polyglycols; or sulphated fatty acid alkanolamides.

As regards nonionic emulsifiers, they can be selected from: polyalcohol fatty esters, fatty acid alkanolamides, polyethylene oxides, oxyethylenated alcohols and alkylphenols, or oxyethylenated and sulphated alcohols and alkylphenols.

These emulsifiers are preferably present in the emulsion in a proportion of approximately 0.1 to 3% by weight with respect to the weight of the monomers.

As regards the monomers, they are monomers as described above in the context of the definition of the claimed composite particles.

These monomers are present in a proportion of 5 to 55% by weight in the aqueous emulsion.

The polymerization reaction is carried out in the presence of an initiator. The latter is generally incorporated in a proportion of approximately 0.05 to 4.5% by weight and preferably in a proportion of 0.1 to 2% by weight of the monomers. Of course, the initiator under consideration is soluble in an aqueous or aqueous/alcoholic medium. Mention may in particular be made, by way of illustration of these initiators, of those selected from: aqueous hydrogen peroxide solution, alkaline persulphates, diazo derivatives, tert-butyl hydroperoxide and redox systems based on an oxidizing agent (aqueous hydrogen peroxide, organic peroxides and organic hydroperoxides) and on a reducing agent (alkaline sulphites, alkaline bisulphites and amines).

Other reactants conventionally employed in radical polymerization can also be considered in the context of the present invention. For example, a crosslinking agent and/or a chain-limiting agent can be introduced into the polymerization mixture. The latter can generally be present at up to 3% and preferably 1% by weight of the monomers. This chain-limiting agent can be a halogenated hydrocarbon, a $C_1$–$C_4$ aliphatic alcohol or a mercaptan.

The operating conditions in carrying out the polymerization of course depend directly on the nature of the monomers under consideration and on the initiator used. However, by way of indication, the polymerization can generally be carried out at a temperature of between approximately 0°C. and 100°C. and preferably between approximately 50°C. and 85°C.

On conclusion of the radical emulsion polymerization, an aqueous dispersion of organic particles is obtained.

According to the first alternative form, the incorporation of the active material is carried out in conjunction with the radical polymerization of the monomers. To this end, the hydrophobic active material is dissolved in the monomers prior to their aqueous, alcoholic or aqueous/alcoholic emulsification and then to their radical polymerization.

According to the second alternative form, which corresponds to the preferred form of the invention, the hydrophobic active material is introduced on conclusion of the radical polymerization of the monomers. In this specific case, its incorporation within the organic particles is carried out by bringing the said organic particles, in aqueous, alcoholic or aqueous/alcoholic dispersion, into contact with the said active material, if appropriate dissolved in a transfer solvent.

Within the meaning of the invention, a transfer solvent denotes a solvent capable of promoting the adsorption of the active material which it comprises by the composite particles of organic polymer. This adsorption can be reflected in particular by a phenomenon of swelling of the said particles under the effect of their permeability with regard to the transfer solvent.

Mention may in particular be made, as transfer solvent capable of being employed according to the invention, of: aromatic derivatives (toluene, ethyl-benzene), chlorinated aromatic derivatives (trichloro-benzene), aliphatic and cyclic hydrocarbons (heptane, dodecane, cyclohexane, decalin, and the like), dialkyl ethers, alcohols (propanol, pentanol, cyclohexanol, and the like), esters (methyl propionate, ethyl acetate, mixture of methyl glutamate/adipate/succinate, "RPDE"), ketones (methyl ethyl ketone, cyclohexanone), chlorinated aliphatic derivatives (dichloromethane) and silicones.

Of course, the choice of the transfer solvent must be made with consideration being given to the nature of the active material to be dissolved and the nature of the polymer to be permeabilized.

Thus it is that, in certain circumstances, the presence of such a transfer agent may prove to be unnecessary. This is because some active materials can possess, in themselves, the property of penetrating into the said particles.

In order to promote the swelling of the said particles, the reaction mixture can be heated. The choice of the temperature is related directly to the nature of the polymer constituting the particles. Preferably, a temperature greater than the glass transition temperature of the polymer is favoured in order to promote the expansion of the polymer chains. In the specific case where a transfer agent is not employed, it is preferable in terms of efficiency of incorporation to continuously add the active material to the reaction mixture.

The active material, in solution or not in solution in a transfer solvent, and the polymer particles, in suspension, are preferably brought into contact with stirring at a temperature of between approximately 20 and 90° C.

The adsorption of the active material by the polymer particles is regarded as complete after 5 to 6 hours. The increase in the size of the polymer particles reflects the degree of incorporation.

On conclusion of the first stage of the process and whatever the alternative adsorption form used, particles based on an organic polymer comprising a hydrophobic active material for which the level of dry matter can vary between 5 and 70% are obtained.

The organic particles with active materials generally exhibit a size of between 0.03 and 10 $\mu$m and preferably between 0.1 and 1 $\mu$m.

At the end of this first stage, the transfer solvent can, if appropriate, be removed prior to the addition of the alkaline earth metal salt(s) from which the intermediate layer derives.

This solvent can be removed by any conventional method in so far as the latter is not such as to affect the stability of polymer particles. A vacuum evaporation of the said transfer solvent can be carried out, for example. However, this removal stage may, in some cases, not prove to be necessary.

As regards the stability of the dispersion of polymer particles incorporating the hydrophobic active material, it may, if appropriate, be advantageous to strengthen it in order in particular to prevent any risk of flocculation during the following stages.

To this end, one or more stabilizing agent(s) of polyethoxylated alkylphenol, polyethylene glycol or polyvinylpyrrolidone type can be added to the aqueous, alcoholic or aqueous/alcoholic dispersion obtained on conclusion of the first stage of the claimed process before it is brought into contact with the soluble alkaline earth metal salt(s).

This stabilizer can be incorporated in a proportion of approximately 0.1 to 5% and preferably of up to 2% by weight with respect to the weight of the said dispersion on a dry basis.

The dispersion of organic particles which is thus obtained is subsequently brought into contact with an alkaline earth metal salt as defined above. The corresponding oxide or hydroxide is deposited by in situ precipitation via the addition of a base.

To this end, the alkaline earth metal salt is first of all dissolved in the liquid phase of the dispersion of polymer particles.

The alkaline earth metal salt is preferably a halide, such as the chloride, or a sulphate. It is more preferably a calcium and/or magnesium chloride or sulphate.

The pH of the liquid phase thus obtained is increased by addition of a base until the appearance of the phenomenon of precipitation of the alkaline earth metal oxide or hydroxide.

Bases of sodium hydroxide, potassium hydroxide or aqueous ammonia type are especially suitable for the invention.

It is clear that the amount of alkaline earth metal salt employed depends directly on the thickness of the deposit of alkaline earth metal oxide or hydroxide desired.

By way of indication, this amount can vary between 0.05% and 3% by weight, expressed with regard to the weight of dry matter in the aqueous, alcoholic or aqueous/alcoholic polymer dispersion to be treated.

If appropriate, it may be necessary to adjust the other parameters of this operation, namely time and temperature, for example, in order for an untroubled precipitation of the said inorganic deposit to be favoured. These adjustments come within the competence of a person skilled in the art.

On conclusion of this operation of depositing an intermediate layer, the deposition of the inorganic external coating is subsequently carried out.

To this end, a silicon, aluminium, zirconium and/or transition metal salt which is soluble in the liquid phase of the dispersion of organic polymer particles, which particles comprise the hydrophobic active material and are covered at least partially with a layer composed of at least one alkaline earth metal hydroxide, is brought into contact in the liquid phase of the said dispersion with an agent capable of reacting with the said soluble salt to form a precipitate composed of the corresponding oxide or hydroxide.

The soluble salts preferably employed are selected from alkali metal silicates, alkali metal aluminates, or oxychlorides, chlorides, nitrates or sulphates of aluminium, of zirconium or of a transition metal as defined above.

The precipitating agent can be selected from acidic or basic compounds. Mention may more particularly be made, by way of indication of the precipitating agents which are suitable for the invention, of phosphoric acid, sulphuric acid, acetic acid, alkali metal hydroxides, aqueous ammonia and carbon dioxide.

The amounts of soluble salt and precipitating agent are generally adjusted so as to obtain an external coating with a thicknessof 1 to 300 nm and preferably of 5 to 100 nm.

This precipitation operation is carried out while keeping the pH of the medium in a range which makes possible maximum precipitation of the oxide or hydroxide. This pH range is generally between 8 and 11. This pH is preferably kept constant between 8 and 11.

The introduction of the salt into the dispersion is carried out so as to prevent the medium becoming supersaturated with salts. In other words, the formation of "outsize" aluminium, silicon, zirconium or transition metal particles is avoided.

This is achieved by controlling in particular the throughput for introduction of the said salt, which a person skilled in the art is in a position to do by carrying out simple routine tests.

The precipitation temperature is preferably itself also controlled. It is generally between 20 and 95° C. and preferably between 20 and 75° C.

The precipitation operation takes place more particularly with stirring.

Furthermore, the process for the preparation of suspensions of composite particles is carried out at atmospheric pressure, although higher or lower pressures are not excluded.

This stage is preferably carried out by employing an alkali metal silicate and an acid as precipitating agent, very particularly sulphuric acid or carbon dioxide.

This operation is preferably carried out at a temperature of 40 to 60°C. while maintaining the pH at a value of 8 to 10.

The resulting composite particles are subsequently dried.

Drying can take place directly on the suspension obtained.

It is possible to dry the particles of the said medium according to conventional methods, such as, for example, centrifuging.

It is pointed out that this second possibility is particularly advantageous in the case where it is desired to subject the composite particles to a surface treatment prior to drying.

This treatment consists, as a general rule, in resuspending the composite particles and then introducing, into the suspension, at least one organic compound, such as stearic acid, stearates or polysiloxane oils, inter alia.

This type of pretreatment makes it possible to prevent, if necessary, the agglomeration of the composite particles during this drying stage. It likewise makes it possible to confer specific properties on the particles, such as, for example, a hydrophobic nature. This treatment also makes it possible to render the composite particles compatible with the medium into which they will subsequently be introduced.

The composite particles obtained can also be subjected to a maturing stage. This operation can consist in heating the said particles at a temperature compatible with their stability, preferably between 40 and 60° C.

This maturing can be carried out for at least one hour.

According to a specific embodiment of the invention, the separation of the composite particles from the reaction mixture and their drying are carried out by atomization, that is to say by spraying the mixture into a hot atmosphere (spray drying). The atomization can be carried out by means of any sprayer known per se, for example with a spray nozzle of shower head or other type. It is also possible to use atomizers known as rotary atomizers. Reference may in particular be made, with regard to the various spraying techniques which can be employed in the preceding process, to the standard work by Masters entitled "Spray Drying" (second edition, 1976, published by George Godwin, London).

It should be noted that it is also possible to carry out the atomization-drying operation by means of a flash reactor, for example of the type disclosed in particular in French Patent Applications Nos. 2,257,326, 2,419,754 and 2,431,321.

The claimed particles or the particles obtained on conclusion of the claimed process are particularly advantageous in the conditioning of active materials. with a hydrophobic nature.

As mentioned above, due to their inorganic casing, the adhesion of which is strengthened at the organic core by virtue of the presence of an intermediate layer, they guarantee better protection of the active material with respect to the external environment. Thus encapsulated, the active material is better protected against any modification in temperature, pH, UV radiation and chemicals capable of appearing in the external environment.

Likewise, the encapsulation according to the invention guarantees, to the user, protection with regard to the encapsulated active material and to its side effects, which can be expressed in particular with regard to smell, appearance or corrosion.

Finally, through the choice of the constituents of the external coating and of the intermediate layer and of their respective thicknesses, it proves to be possible to adjust the diffusion of the active material present in the composite particles.

Another subject-matter of the present invention is the use of the composite particles claimed or obtained according to the invention in the food, cosmetics, plant-protection and pharmaceutical industries.

They are very particularly of use in the encapsulation of cosmetically active materials.

The examples and figure submitted below are presented by way of illustration and without implied limitation of the present invention.

FIG. 1: Transmission electron microscopy photography of latex particles incorporating a UV stabilizer which are coated with an inorganic shell (scale of 0.11 μm per 1 cm).

EXAMPLE 1

Incorporation of a UV Stabilizer in a Latex-type Polymer

The latex is considered to be Rhodopas SB112®. It is an aqueous dispersion of a functionalized styrene-butadiene copolymer with a particle size of 0.19 μm (determined by light scattering) and a solids content of 56%.

1250 g of polymer, expressed as dry weight, are dispersed in 794 g of water in a 4 l reactor with stirring at 210 revolutions/minute and at a temperature of 85° C. 500 g of Parsol MCX® (2-ethylhexyl methoxycinnamate, sold as UV-B stabilizer) are continuously added thereto over 2 hours. At the end of the addition, the mixture is subjected to a maturing stage at 85° C. for 8 hours. The dispersion is subsequently cooled to room temperature and filtered through a 112 μm sieve. The particles obtained have a size of 0.21 μm.

EXAMPLE 2

Preparation of Latex Particles Comprising an Active Material Which are Coated With a Silica Coating Starting Materials The latex dispersion prepared according to Example 1

Calcium chloride, Prolabo, Normapur

Surfactant: Antarox B 848® (polyethoxylated alcohol) (RP-Gerronazzo®)

Sodium silicate (d: 1.33)

NaOH, 1 mol/l $H_2SO_4$, 1 mol/l

| Overall composition: | |
|---|---|
| Latex incorporating Parsol MCX ® | 145 g (80 g dry) |
| $CaCl_2.2H_2O$ | 2.114 g (dissolved in 98 g of water) |
| Antarox B848 ® | 3.2 g pure (10% aqueous solution) |
| Sodium silicate | 238.88 g |
| Purified water | 1007 g |
| NaOH, 1 mol/l | q.s. for pH 9 |
| $H_2SO_4$, 1 mol/l | q.s. for regulation pH 9 (approximately 310 g) |

Procedure

The modified Latex and 748 g of purified water are added to a 2 litre reactor. The aqueous solution of Antarox B 848® is subsequently added and the mixture is stirred for 1 hour. The calcium chloride is subsequently added in the form of an aqueous solution (addition with a throughput of 4.9 ml/min). After the addition of calcium chloride, the pH is adjusted to 9 with sodium hydroxide solution. The reaction mixture is subsequently heated to 50°C. After the temperature and the pH have stabilized, the aqueous sodium silicate solution (throughput: 1.6 ml/min) and the sulphuric acid solution are added (both introduced at constant pH). After the introduction of the silicate, maturing is carried out for 2 hours at 50°C.

After cooling, the particles are separated by centrifuging and the cake is washed 3 times and then redispersed in an aqueous medium.

It is observed by transmission electron microscopy, TEM, that the latex particles are coated with a silica shell of the order of about 10 nanometers. FIG. 1 is a photographic representation of the particles obtained. After the particles obtained above have been calcined at 600°C., hollow silica particles of approximately 150 nm are obtained. These results clearly confirm that an inorganic shell about an organic core is obtained.

What is claimed is:

1. Composite particles comprising at least
   one core comprising at least one organic polymer in which is dispersed at least one hydrophobic, active material, wherein the hydrophobic active material is a cosmetic, pharmaceutical, food or plant-protection material,
   one external coating comprising at least one oxide and/or hydroxide of aluminum, of silicon, of zirconium and/or of a transition metal and
   one intermediate layer, present at least partially between the core and the external coating and comprising at least one alkaline earth metal hydroxide.

2. Composite particles according to claim 1, wherein the organic polymer derives from one or more water-immiscible ethylenically unsaturated monomers which can be polymerized by the radical route.

3. Composite particles according to claim 1, wherein the organic polymer derives from one or more water-immiscible ethylenically unsaturated monomers which can be polymerized by the radical route, wherein said ethylenically unsaturated monomers are vinylaromatic monomers, alkyl esters of α,β-ethylenically unsaturated acids, vinyl esters of carboxylic acids, vinyl or vinylidene halides, conjugated aliphatic dienes, α,β-ethylenically unsaturated nitrites, or a mixture thereof.

4. Composite particles according to claim 1, wherein the organic polymer derives from one or more water-immiscible ethylenically unsaturated monomers which can be polymerized by the radical route, wherein said ethylenically unsaturated monomers are styrene, butadiene, acrylonitrile, chloroprene, vinyl or vinylidene chloride, isoprene, isobutylene, vinyl acetate, propylene, butylene, vinylpyrrolidone, or a mixture thereof.

5. Composite particles according to claim 1, wherein the organic polymer additionally comprises up to 8% of at least one comonomer carrying ionogenic groups which can be polymerized by the radical route.

6. Composite particles according to claim 1, wherein the organic polymer additionally comprises up to 8% of at least one comonomer carrying ionogenic groups which can be polymerized by the radical route, wherein said comonomer is one or more α,β-ethylenically unsaturated carboxylic acids, sulphonated ethylenic monomers, hydroxyalkyl esters of α,β-ethylenically unsaturated acids, amides of α,β-ethylenically unsaturated acids, aminoesters of α,β-ethylenically unsaturated acids, or a mixture thereof.

7. Composite particles according to claim 1, wherein the organic polymer additionally comprises up to 8% of at least one comonomer carrying ionogenic groups which can be polymerized by the radical route, wherein said comonomer is one or more acrylic, methacrylic, itaconic, maleic, crotonic, parastyrenesulphonic, vinylsulphonic, 2-methacryloyloxyethylsulphonic, 2-acrylamido-2-methylpropanesulpbonic or vinylbenzenesulphonic acids, hydroxyethyl acrylate, hydroxyethyl methacrylate, acrylamide, methacrylamide, diethyl-aminoethyl methacrylate, or a mixture thereof.

8. Composite particles according to claim 1, wherein the organic polymer constituting the core of the said particles is one or more polystyrenes or copolymers of styrene and of acrylic esters, of styrene and of butadiene or of styrene, of butadiene and of acrylamide.

9. Composite particles according to claim 1, wherein the organic polymer has a glass transition temperature between −100°C. and 150° C.

10. Composite particles according to claim 1, wherein the organic polymer has a glass transition temperature between −100°C. and 100°C.

11. Composite particles according to claim 1, wherein the diameter of the core of organic polymer incorporating the active material is between approximately 0.03 and 10 μm.

12. Composite particles according to claim 1, wherein the external coating is composed of a single layer based on at least one oxide and/or hydroxide of aluminum, of silicon, of zirconium and/or of a transition metal.

13. Composite particles according to claim 1, wherein the external coating is composed of at least two layers based on at least one oxide and/or hydroxide of aluminum, of silicon, of zirconium and/or of a transition metal.

14. Composite particles according to claim 1, wherein the external coating comprises an oxide and/or a hydroxide of several elements in the same layer.

15. Composite particles according to claim 1, wherein the external coating comprises an oxide and/or a hydroxide of titanium, manganese, iron, cobalt, nickel, copper, or a mixture thereof.

16. Composite particles according to claim 1, wherein the external coating comprises at least one oxide and/or hydroxide of silicon, aluminum, titanium or zirconium, or a mixture thereof.

17. Composite particles according to claim 1, wherein the intermediate layer comprises one or more alkaline earth metal hydroxides, wherein said alkaline earth metal hydroxide is calcium hydroxide, magnesium hydroxide, or a mixture thereof.

18. Composite particles according to claim 1, wherein the total thickness of the coating applied at the surface of the organic core and comprising one or more layers based on at least one oxide and/or hydroxide of aluminum, of silicon, of zirconium and/or of a transition metal and a layer of at least one alkaline earth metal hydroxide is at most 300 nm.

19. Composite particles according to claim 1, wherein the thickness of the coating applied at the surface of the organic core and comprising one or more layers based on at least one oxide and/or hydroxide of aluminum, of silicon, of zirconium and/or of a transition metal and a layer of at least one alkaline earth metal hydroxide is at least 1 nm.

20. Composite particles according to claim 1, the thickness of the coating applied at the surface of the organic core and comprising one or more layers based on at least one oxide and/or hydroxide of aluminum, of silicon, of zirconium and/or of a transition metal and a layer of at least one alkaline earth metal hydroxide is between 1 and 300 nm.

21. Composite particles according to claim 1, the thickness of the coating applied at the surface of the organic core and comprising one or more layers based on at least one oxide and/or hydroxide of aluminum, of silicon, of zirconium and/or of a transition metal and a layer of at least one alkaline earth metal hydroxide is between 5 and 100 nm.

22. Composite particles according to claim 1, wherein the hydrophobic active material dispersed in the organic polymer core is one or more organic UV stabilisers, essential or therapeutic oils, fragrances, cosmetic colorants, or a mixture thereof.

23. Composite particles according to claim 1, wherein the active material is dispersed within the organic polymer in a proportion of 0.1 to 200% by weight, expressed with respect to the weight of dry polymer.

24. Composite particles according to claim 1, which exhibit a specific surface of between approximately 1 and 200 $m^2/g$.

25. Composite particles according to claim 1, having their diameter which varies between approximately 0.02 and 6 μm.

26. A process of use in the preparation of composite particles comprising at least
one core comprising at least one organic polymer in which is dispersed at least one hydrophobic, active material, wherein the hydrophobic active material is a cosmetic, pharmaceutical, food or plant-protection material,
one external coating comprising at least one oxide and/or hydroxide of aluminum, of silicon, of zirconium and/or of a transition metal and
one intermediate layer, present at least partially between the core and the external coating and comprising at least one alkaline earth metal hydroxide and comprising at least:
the incorporation of at least one hydrophobic active material in particles based on at least one organic polymer, said particles being in aqueous, alcoholic or aqueous/alcoholic dispersion and, optionally formed in conjunction with the incorporation of said active material,
the dissolution of at least one alkaline earth metal salt in the liquid phase of the dispersion of polymer particles, which particles comprise at least one hydrophobic active material and are obtained according to the preceding stage, the addition of a base in a sufficient amount to precipitate a layer of oxide or of hydroxide of said alkaline earth metal at the surface of said particles, the bringing of at least one water-soluble silicon, aluminum, zirconium and/or transition metal salt into contact, in the liquid phase of the particle dispersion obtained on conclusion of the preceding stage, with at least one agent capable of reacting with said soluble salt to form a precipitate composed of the corresponding oxide or hydroxide at the surface of said particles and, the drying and the recovery of the composite particles thus obtained.

27. The process according to claim 26, wherein the particles based on at least one organic polymer are obtained by aqueous, alcoholic or aqueous/alcoholic radical emulsion polymerization of water-immiscible and polymerizable ethylenically unsaturated monomers.

28. The process according to claim 26, wherein the organic polymer derives from one or more water-immiscible ethylenically unsaturated monomers which can be polymerized by the radical route.

29. The process according to claim 26, wherein the organic polymer derives from one or more water-immiscible ethylenically unsaturated monomers which can be polymerized by the radical route, wherein said ethylenically unsaturated monomers are vinylaromatic monomers, alkyl esters of α,β-ethylenically unsaturated acids, vinyl esters of carboxylic acids, vinyl or vinylidene halides, conjugated aliphatic dienes, α,β-ethylenically unsaturated nitrites, or a mixture thereof.

30. The process according to claim 26, wherein the organic polymer derives from one or more water-immiscible ethylenically unsaturated monomers which can be polymerized by the radical route, wherein said ethylenically unsaturated monomers are styrene, butadiene, acrylonitrile, chloroprene, vinyl or vinylidene chloride soprene, isobutylene, vinyl acetate, propylene, butylene, vinylpyrrolidone, or a mixture thereof.

31. The process according to claim 26, wherein the organic polymer additionally comprises up to 8%, of at least one comonomer carrying ionogenic groups which can be polymerized by the radical route.

32. The process according to claim 26, wherein the organic polymer additionally comprises up to 8%, of at least one comonomer carrying ionogenic groups which can be polymerized by the radical route, wherein said comonomer is one or more α,β-ethylenically unsaturated carboxylic acids, sulphonated ethylenic monomers, hydroxyalkyl esters of α,β-ethylenically unsaturated acids, amides of α,β-ethylenically unsaturated acids, aminoesters of α,β-ethylenically unsaturated acids, or a mixture thereof.

33. The process according to claim 26, wherein the organic polymer additionally comprises up to 8%, of at least one comonomer carrying ionogenic groups which can be polymerized by the radical route, wherein said comonomer is one or more acrylic, methacrylic, itaconic, maleic, crotonic, parastyrenesulphonic, vinylsulphonic, 2-methacryloyloxyethylsulphonic, 2-acrylamido-2-methylpropanesulphonic or vinylbenzene-sulphonic acids, hydroxyethyl acrylate, hydroxyethyl methacrylate, acrylamide, methacrylamide, diethylaminoethyl methacrylate, or a mixture thereof.

34. The process according to claim 26, wherein the particles based on at least one organic polymer are obtained by aqueous, alcoholic or aqueous/alcoholic radical emulsion polymerization of water-immiscible with said polymerizable ethylenically unsaturated monomers with said radical polymerization being carried out in the presence of at least one emulsifier.

35. The process according to claim 26, wherein the incorporation of the hydrophobic active material is carried out in conjunction with the radical emulsion polymerization of the monomers constituting the organic polymer.

36. The process according to claim 26, wherein the incorporation of the hydrophobic active material is carried out in conjunction with the radical emulsion polymerization of the monomers, constituting the organic polymer and by dissolving it in the monomers prior to their aqueous, alcoholic or aqueous/alcoholic emulsification and then to their radical polymerization.

37. The process according to claim 26, wherein the hydrophobic active material is introduced on conclusion of the radical polymerization of the monomers, constituting the organic polymer.

38. The process according to claim 26, wherein the incorporation of the hydrophobic active material within the organic particles is carried out by bringing said organic particles, in aqueous, alcoholic or aqueous/alcoholic dispersion, into contact with said active material, optionally dissolved in a transfer solvent.

39. The process according to claim 26, wherein the incorporation of the hydrophobic active material within the organic particles is carried out by bringing said organic particles, in aqueous, alcoholic or aqueous/alcoholic dispersion, into contact with said active material, optionally dissolved in a transfer solvent, said transfer solvent being selected from the group consisting of ketones, aromatic derivatives, chlorinated aromatic derivatives, dialkyl ethers, alcohols, esters, chlorinated aliphatic derivatives and silicones.

40. The process according to claim 26, wherein the incorporation of the hydrophobic active material within the organic particles is carried out by bringing said organic particles, in aqueous, alcoholic or aqueous/alcoholic dispersion, into contact with said active material, optionally dissolved in a transfer solvent with said transfer solvent being removed prior to the addition of the alkaline earth metal salt or salts from which the intermediate layer derives.

41. The process according to claim 26, wherein the incorporation of the hydrophobic active material within the organic particles is carried out by bringing said organic particles, in aqueous, alcoholic or aqueous/alcoholic dispersion, into contact with said active material, optionally dissolved in a transfer solvent with said transfer solvent being removed prior to the addition of the alkaline earth metal salt or salts from which the intermediate layer derives and with one or more stabilizing agent(s) of polyethoxylated alkylphenol, polyethylene glycol or polyvinylpyrrolidone being added to the aqueous, alcoholic or aqueous/alcoholic dispersion obtained on conclusion of the first stage before it is brought into contact with the soluble alkaline earth metal salt(s).

42. The process according to claim 26, wherein the particles based on at least one organic polymer are obtained by aqueous, alcoholic or aqueous/alcoholic radical emulsion polymerization of water-immiscible and polymerizable ethylenically unsaturated monomers and with the alkaline earth metal salt dissolved in the second stage of the process being a calcium and/or magnesium chloride or sulphate.

43. The process according to claim 26, wherein the silicon, aluminum, zirconium and/or transition metal salt dissolved in the fourth stage of the process is one or more alkali metal silicates, alkali metal aluminates, or oxychlorides, chlorides, nitrates or sulphates of aluminum, of zirconium or of a transition metal, or a mixture thereof.

44. The process according to claim 26, wherein the precipitating agent employed in the fourth stage of the process is phosphoric acid, sulphuric acid, acetic acid, alkali metal hydroxides, aqueous ammonia, carbon dioxide, or a mixture thereof.

45. The process according to claim 26, wherein the amounts of soluble salt and of precipitating agent are adjusted so as to obtain an external coating with a thickness of 1 to 300 nm.

46. The process according to claim 26, wherein the operation of precipitating the oxide and/or hydroxide of silicon, of aluminum, of zirconium and/or of a transition metal is carried out while maintaining the pH between 8 and 11.

47. The process according to claim 26, wherein the fourth stage employs an alkali metal silicate and an acid as precipitating agent.

48. The process according to claim 26, wherein the fourth stage employs an alkali metal silicate and sulphuric acid or carbon dioxide as precipitating agent.

49. The process according to claim 26, wherein the composite particles are subjected to a surface treatment prior to their drying.

50. The process according to claim 26, wherein the composite particles obtained are additionally subjected to maturing.

* * * * *